US007285388B1

(12) United States Patent
Murphy et al.

(10) Patent No.: US 7,285,388 B1
(45) Date of Patent: Oct. 23, 2007

(54) METHODS FOR IDENTIFICATION OF ALPORT SYNDROME

(75) Inventors: Keith E. Murphy, College Station, TX (US); Ashley G. Davidson, College Station, TX (US); George E. Lees, College Station, TX (US)

(73) Assignee: Merlogen, LLC, College Station, TX (US)

( * ) Notice: Subject to any disclaimer, the term of this patent is extended or adjusted under 35 U.S.C. 154(b) by 0 days.

(21) Appl. No.: 11/423,650

(22) Filed: Jun. 12, 2006

Related U.S. Application Data

(60) Provisional application No. 60/790,115, filed on Apr. 7, 2006.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search ............... None
See application file for complete search history.

(56) References Cited

U.S. PATENT DOCUMENTS

| | | | |
|---|---|---|---|
| 4,582,788 | A | 4/1986 | Erlich |
| 4,656,127 | A | 4/1987 | Mundy |
| 4,683,194 | A | 7/1987 | Saiki et al. |
| 4,683,202 | A | 7/1987 | Mullis |
| 4,988,617 | A | 1/1991 | Landegren et al. |
| 5,143,854 | A | 9/1992 | Pirrung et al. |
| 5,202,231 | A | 4/1993 | Drmanac et al. |
| 5,324,633 | A | 6/1994 | Fodor et al. |
| 5,405,783 | A | 4/1995 | Pirrung et al. |
| 5,424,186 | A | 6/1995 | Fodor et al. |

FOREIGN PATENT DOCUMENTS

| | | |
|---|---|---|
| EP | 50424 | 4/1982 |
| EP | 84796 | 8/1983 |
| EP | 201184 | 12/1986 |
| EP | 237362 | 9/1987 |
| EP | 258017 | 3/1988 |
| WO | WO 89/10977 | 11/1989 |
| WO | WO 90/15070 | 12/1990 |
| WO | WO 91/02087 | 2/1991 |
| WO | WO 91/17239 | 11/1991 |
| WO | WO 92/10588 | 6/1992 |
| WO | WO 92/15712 | 9/1992 |
| WO | WO 92/16655 | 10/1992 |
| WO | WO 93/17126 | 9/1993 |
| WO | WO 94/11530 | 5/1996 |

OTHER PUBLICATIONS

Longo et al. (Kidney International, vol. 61, pp. 1947-1956, 2002).*
Pescucci et al. (Kidney International, vol. 65, pp. 1598-1603, 2004).*
Wiersma et al. (DNA Sequence, vol. 16, No. 4, pp. 241-251, Aug. 2005).*
Daghet al. (Human Mutation, Mutation in Brief #536, 2002).*
Genbank Accession No. AY263363, Canis familiaris collagen typ IV alpha 4 chain mRNA, Nov. 29, 2005.*
Wiersma, J. of heredity, vol. 96, No. 7, pp. 739-744, 2005.*
Baker and Parker "Nonsense-mediated mRNA decay:terminating erroneous gene expression", *Curr Opin Cell Biol.*, 16(3):293-9 (2004).
Barany, "Genetic Disease Detection and DNA Amplification Using Cloned Thermostable Ligase", *Proc. Natl. Acad. Sci. USA*, 88:189-193 (1991).
Barany, "The Ligase Chain Reaction (LCR) in a PCR World" *PCR Methods and Applications*, 1:5-16 (1991).
Barany, et al., "Cloning, Overexpression and Nucleotide Sequence of a Thermostable DNA ligase-encoding Gene", *Gene*, 109:1-11 (1991).
Barker, et al. "Identification of mutations in the COL4A5 collagen gene in Alport syndrome", *Science*, 248(4960):1224-7 (1990).
Beattie, et al., "Advances in Genosensor Research", *Clin. Chem.*, 41(5):700-09 (1995).
Cardullo, et al., "Detection of Nucleic Acid Hybridization by Nonradiative Fluorescence Resonance Energy Transfer", *Proc. Nat. Acad. Sci. USA*, 85:8790-94 (1988).
Chetverin, et al., "Sequencing of Pools of Nucleic Acids on Oligonucleotide Arrays", *BioSystems*, 30:215-31 (1993).
Cox, et al. "Genetic cause of X-linked Alport syndrome in a family of domestic dogs", *Mamm Genome*, 14(6):396-403 (2003).
Delahunty, et al., "Testing the feasibility of DNA typing for human identification by PCR and an oligonucleotide ligation assay", *Am. J. Hum. Genet.*, 58:1239-1246 (1996).
Ding, et al. "Autosomal recessive Alport syndrome:mutation in the COL4A3 gene in a woman with Alport syndrome and posttransplant antiglomerular basement membrane nephritis", *J Am Soc Nephrol*, 5(9):1714-7 (1995).

(Continued)

*Primary Examiner*—Jeanine A. Goldberg
(74) *Attorney, Agent, or Firm*—Pabst Patent Group LLP

(57) ABSTRACT

Animals with mutations in COL4a4 present with autosomal recessive Alport Syndrome (ARAS). Through sequencing of COL4a4, the mutation causative for ARAS in the English Cocker Spaniel (ECS) has been identified. The resulting protein is severely truncated due to a premature stop codon in exon 3. This nonsense mutation occurs in the 7S domain and also causes the loss of the entire collagenous and NC1 domains of the protein. Methods for the identification of animals that harbor a mutation in the COL4a4 gene are described. Mutations in the COL4a4 gene can be identified from any biological sample such as a cell or tissue that contains genomic DNA. Methods for identifying single nucleotide polymorphisms (SNPs) that are inherited with the disease are also described. A microsatellite marker that segregates with ARAS is also described that was identified using linkage disequilibrium mapping.

4 Claims, 2 Drawing Sheets

OTHER PUBLICATIONS

EFRON, "Bootstrap Methods:Another look at the Jackknife", *Ann Statistics,* 7:1-26 (1979).

English and Winter "Renal cortical hypoplasia in a dog", *Aust Vet J.* 55(4):181-3 (1979).

Freudiger, "Die kongenitale nierenrindenhypoplasie beim bunten cocker-spaniel", *Schweizer Arch Tierheilk,* 107:547-566 (1965).

GU, et al., "Detection of Single Nucleotide Polymorphism", *BioTechniques,* 24:836-837 (1998).

Guatelli, et al., "Isothermal In-Vitro Amplification of Nucleic Acids By a Multienzyme Reaction Modeled After Retroviral Replication", *Proc. Natl. Acad. Sci. USA,* 87:1874-1878 (1990).

Guyon, et al., "A 1-Mb resolution radiation hybrid map of the canine genome", *Proc Natl Acad Sci U S A.*, 100:5296-5301 (2003).

Harvey, et al. "Role of distinct type IV collagen networks in glomerular development and function", *Kidney Int,* 54(6):1857-66 (1998).

Hudson, et al. "Alport's syndrome, Goodpasture's syndrome, and type IV collagen", *N Engl J Med,* 348(25):2543-56 (2003).

Hyun, et al., "Prospects for whole genome linkage disequilibruim mapping in domestic dog breeds", *Mamm. Genome,* 14:640-649 (2003).

Jansen, et al. "Samoyed hereditary glomerulopathy:serial, clinical and laboratory (urine, serum biochemistry and hematology) studies", *Can J Vet Res,* 51(3):387-93 (1987).

Jansen, et al. "Samoyed hereditary glomerulopathy (SHG). Evolution of splitting of glomerular capillary basement membranes", *Am J Pathol,* 125(3):536-45 (1986).

Knebelmann, et al. "Spectrum of mutations in the COL4A5 collagen gene in X-linked Alport syndrome", *Am J Hum Genet ,* 59(6):1221-32 (1996).

Koeman, et al. "[Familial nephropathy in cocker spaniels] ", *Dtsch Tierarztl Wochenschr* 96(4):174-9 (1989).

Kornher, et al., "Mutation Detection Using Nucleotide Analogs that Alter Electrophoretic Mobility", *Nuci. Acids. Res. ,* 17:7779-7784 (1989).

KROOK, "The Pathology of Renal cortical hypoplasia in the dog", *Nord Vet-Med,* 9:161-176 (1957).

Kuppuswamy, et al., "Single Nucleotide Primer Extension to Detect Genetic Diseases:Experimental Applicaiton to Hemophilia B (Factor IX) and Cystic Fibrosis Genes", *Proc. Natl. Acad. Sci. USA,* 88:1143-11747 (1991).

Kuznetsova, et al., "DNA Sequencing by Hybridization with Oligonucleotides Immobilized in Gel. Chemical Ligation as a Method of Expanding the Prospects for the Method", *Mol. Biol.,* 28(20):290-99 (1994).

Kwoh, et al., "Target Amplification Systems in Nucleic Acid-Based Diagnostic Approaches", *Am. Biotechnol. Lab.,* 8:14-25 (1990).

Kwoh, et al., "Transcription-Based Amplification System and Detection of Amplified Human Immunodeficiency Virus Type 1 With a Bead-Based Sandwich Hybridization Format", *Proc. Natl. Acad. Sci. USA,* 86:1173-1177 (1989).

Landegren, et al., "A Ligase-Mediated Gene Detection Technique", *Science,* 241:1077-80 (1988).

Landegren, et al., "DNA Diagnostics-Molecular Techniques and Automation", *Science,* 242:229-237 (1988).

Landegren, et al., "Reading Bits of Genetic Information:Methods for Single-Nucleotide Polymorphism Analysis", *Genome Research,* 8:769-776 (1998).

Lees et al. "New form of X-linked dominant hereditary nephritis in dogs", *Am J Vet Res,* 60(3):373-83 (1999).

Lees, et al. "Early diagnosis of familial nephropathy in English cocker spaniels", *J Am Anim Hosp Assoc,* 34(3):189-95 (1998).

Lees, et al., "A Model of autosomal recessive Alport syndrome in English cocker spaniel dogs", *Kidney Int.,* 54:706-719 (1998).

Lees, et al., "Glomerular ultrastructural findings similar to hereditary nephritis in 4 English cocker spaniels", *J. Vet. Intern. Med.,* 11:80-85 (1997).

Lemmink, et al. "Mutations in the type IV collagen alpha 3 (COL4A3) gene in autosomal recessive Alport syndrome", *Hum Mol Genet,* 3(8):1269-73 (1994).

Lewis, "Review of Progress in Developing Amplification Technologies Which May Compete with Roche Diagnostic Systems Polymerase Chain Reaction (PCR)", *Genetic Engineering News,* 12(9):1, 8-9 (1992).

Livshits, et al., "Dissociation of Duplexes Formed by Hybridization of DNA with Gel-Immobilized Oligonucleotides", *J. Biomolec. Struct. & Dynam.,* 11(4):783-812 (1994).

Lizardi, et al., "Exponential Amplification of Recombinant RNA Hybridization Probes", *Biotechnology,* 6:1197-1202 (1988).

Longo, et al. "COL4A3/COL4A4 mutations:from familial hematuria to autosomal—dominant or recessive Alport syndrome", *Kidney Int,* 61(6):1947-56 (2002).

Lowe, et al. "Radiation hybrid mapping of the canine type I and type IV collagen gene subfamilies", *Funct Integr Genomics,* 3(3):112-6 (2003).

MacDougali, et al. "Control scheme for familial nephropathy in cocker spaniels", *Vet Rec,* 121(6):134 (1987).

Marshall, et al., "Determination of hepatitis C virus genotypes in the United States by cleavase fragment length polymorphism analysis", *Clin. Microbiol.,* 35:3156-3162 (1997).

Mashal, et al., "Detection of mutations by cleavage of DNA heteroduplexes with bacteriophage resolvases", *Nature Genet.,* 9:177-183 (1995).

Maxam, et al., "A New Method for Sequencing DNA", *Proc. Natl. Acad. Sci. USA,* 74:560-564 (1977).

Mochizuki, et al. "Identification of mutations in the alpha 3(IV) and alpha 4(IV) collagen genes in autosomal recessive Alport syndrome", *Nat Genet,* 8(1):77-81 (1994).

Mullis, et al., "Specific Enzymatic Amplification of DNA in Vitro the Polymerase Chain Reaction", *Cold Spring Harbor Symp. Quant. Biol.,* 51:263-274 (1986).

Murray, "Improved Double Stranded Sequencing Using the Linear Polymerase Chain Reaction", *Nucleic Acids Research,* 17:88-89 (1989).

Myers, et al., "Detection of single base substitutions by ribonuclease cleavage at mismatches in RNA:DNA duplexes", *Science,* 230:1242-1246 (1985).

Nickerson, et al., "Automated DNA Diagnostics Using an Elisa-Based Oligonucleotide Ligation Assay", *Proc. Natl. Acad. Sci. USA,* 87:8923-8927 (1990).

Nyren, et al., "Solid Phase DNA Minisequencing by an Enzymatic Luminometric Inorganic Pyrophosphate Detection Assay", *Anal. Biochem.,* 208:171-175 (1993).

O'Donovan, et al., "Blind analysis of denaturing high-performance liquid chromatography as a tool for mutation detection", *Genomics,* 52:44-49 (1998).

Orita, et al., "Detection of Polymorphisms of Human DNA by Gel Electrophoresis as Single-Strand Conformation Polymorphisms", *Proc. Natl. Acad. Sci. USA,* 86:2766-2770 (1989).

Pease, et al., "Light-generated Oligonucleotide Arrays for Rapid DNA Sequence Analysis", *Proc. Natl. Acad. Sci USA,* 91:5022-26 (1994).

Persson, et al. "Renal cortical hypoplasia in dogs:A clinical study on uraemia and secondary hyperparathyroidism", *Acta Vet Scand,* 2:68-84 (1961).

Pescucci, et al., "Autosomal-dominant Alport syndrome:natural history of a disease due to COL4A3 or COL4A4 gene", *Kidney Int,* 65(5):1598-603 (2004).

PFAFFL, "A new mathematical model for relative quantification in real-time RT-PCR", *Nucleic Acids Res,* 29(9):e45 (2001).

Potter, et al. "A suspected case of familial nephropathy in the Cocker Spaniel", *N Z Vet J,* 33(5):65-6 (1985).

Prezant, et al., "Trapped-Oligonucleotide Nucleotide Incorporation (TONI) Assay, a Simple Method for Screening Point Mutations", *Hum. Mutat.,* 1:159-164 (1992).

Prober, et al., "A System for Rapid DNA Sequencing with Fluorescent Chain-Terminating Dideoxynucleotides", *Science,* 238:336-341 (1987).

Ray, et al., "A Highly Polymorphic RFLP Marker in the Canina Transucin .alpha.-1 Subunit Gene", *Animal Genetics,* 27:372-373 (1996).

Ray, et al., "PCR/RFLP Marker in the Canine Opsin Gene", *Animal Genetics,* 27:293-294 (1996).

Ray, et al., "Molecular Diagnostic Test for Ascertainment of Genotype at the Rod Cone Dysplasia (rcd1) Locus in Irish Setters", *Current Eye Research*, 14:243-247 (1995).

Rheault, et al. "Mouse model of X-linked Alport syndrome", *J Am Soc Nephrol*, 15(6):1466-74 (2004).

Robinson, et al., "Familial nephropathy in cocker spaniels", *Aust Vet J*, 62(4):109-12 (1985).

Saiki, et al., Analysis of enzymatically amplified beta-globin and HLA-DQ alpha DNA with allele-specific oligonucleotide probes', *Nature*, 324:163-166 (1986).

Saiki, et al., "Enzymatic Amplification of Beta Globin Genomic Sequences and Restriction Site Analysis for Diagnosis of Sickle Cell Anemia", *Science*, 230:1350-1354 (1985).

Sanger, et al., "DNA Sequencing with Chain-Terminating Inhibitors", *Proc. Natl. Acad. Sci. USA*, 74:5463-5467 (1977).

Sarkar, et al., "Dideoxy fingerprinting (ddE):a rapid and efficient screen for the presence of mutations", *Genomics*, 13:441-443 (1992).

Sokolov, "Primer Extension Technique for the Detection of Single Nucleotide in Genomic DNA", *Nucl. Acids Res.*, 18:3671 (1990).

Steward and MacDougall "Familial nephropathy in the cocker spaniel", *J Small Anim Pract*, 25:15-24 (1984).

Syvanen, et al., "Identification of Individuals by Analysis of Biallelic DNA Markers, Using PCR and Solid-Phase Minisequencing", *Amer. J. Hum. Genet.*, 52:46-59 (1993).

Syvanen, et al., "A Primer-Guided Nucleotide Incorporation Assay in the Genotyping of Apolipoprotein E", *Genomics*, 8:684-692 (1990).

Syvanen, et al., "Convenient and quantitative determination of the frequency of a mutant allele using solid-phase minisequencing:application to aspartylglucosaminuria in Finland", *Genomics*, 12:590-595 (1992).

Thorner, et al. "Samoyed hereditary glomerulopathy. Immunohistochemical staining of basement membranes of kidney for laminin, collagen type IV, fibronectin, and Goodpasture antigen, and correlation with electron microscopy of glomerular capillary basement membranes", *Lab Invest*, 56(4):435-43 (1987).

Ugozzoli, et al., "Detection of Specific Alleles by Using Allele-specific Primer Extension Followed by Capture on Solid Support", *GATA*, 9:107-112 (1992).

Van Der Loop, et al. "Autosomal dominant Alport syndrome caused by a COL4A3 splice site mutation", *Kidney Int*, 58(5):1870-5 (2000).

Vega, et al. "Autosomal recessive Alport's syndrome and benign familial hematuria are collagen type IV disease", *Am. J Kidney Dis*, 42:952-959 (2003).

Walker, et al., "Isothermal In-Vitro Amplification of DNA By a Restriction Enzyme—DNA Polymerase System", *Proc. Natl. Acad. Sci. USA*, 89:392-396 (1992).

Walker, et al., "Strand Displacement Amplification—An Isothermal, In Vitro DNA Amplification Technique", *Nucleic Acids Res.*, 20:1691-1696 (1992).

Wang, et al., "PCR/RFLP Marker in the Canine Transducin-.gamma. Gene (GNGT1)", *Animal Genetics*, 28:319-320 (1997).

White, et al., "Detecting single base substitutions as heteroduplex polymorphisms", *Genomics*, 12:301-306 (1992).

Zeiss, et al., "A Highly Polymorphic RFLP Marker in the Canine Retinitis Pigmentosa GTPase Regulator (RPGR) Gene", *Animal Genetics*, 29:409 (1998).

Zheng, et al. "Canine X chromosome—linked hereditary nephritis:a genetic model for human X-linked hereditary nephritis resulting from a single base mutation in the gene encoding the alpha 5 chain of collagen type IV", *Proc Natl Acad Sci U S A*, 91(9):3989-93 (1994).

* cited by examiner

METHODS FOR IDENTIFICATION OF ALPORT SYNDROME

This application claims priority to U.S.S.N. 60/790,115 filed Apr. 7, 2006.

BACKGROUND OF THE INVENTION

The present invention is generally in the field of genetic testing in dogs, and is specifically a genetic test for the mutation that causes Alport Syndrome (AS) or for a marker associated with the mutation.

Alport Syndrome (AS) is hereditary progressive glomerular nephritis which affects both humans and several breeds of the domestic dog. This disease is caused by mutations in the genes that encode certain proteins in the type IV collagen family. The type IV collagen family includes six distinct chains (a1-a6) which are major constituents of mammalian basement membranes throughout the body. AS specifically affects the glomerular basement membrane (GBM) of the kidney, causing a distinctive multilaminar splitting of the GBM ultrastructure, characteristic to the disease. These defects in the GBM contribute to the development of hematuria, proteinuria, and progressive renal injury which eventually lead to end stage renal disease (ESRD). Some human cases of AS have been reported to also be associated with hearing loss, ocular lesions and, in rare instances, leiomyomatosis.

AS is known to be transmitted genetically by three different mechanisms: X-linked (XL), autosomal recessive (AR), and autosomal dominant (AD). X-linked AS (XLAS) is caused by mutations in COL4a5 and is the most common form of AS, accounting for about 85% of human cases. Over 300 mutations in this gene causing human XLAS have been identified. In both the human and the dog, COL4a5 is located on the X chromosome. Autosomal recessive AS (ARAS) occurs less frequently, accounting for about 15% of human AS cases and is caused by loss of either COL4a3 or COL4A4. However, the causative mutations in these genes have not been identified. These genes are located on human chromosome 2 and canine chromosome 25. Mutations in COL4a3 or COL4a4 have also been reported to cause autosomal dominant AS (ADAS), which is the rarest form of AS, accounting for less than 5% of human cases.

Type IV collagen genes each encode a distinct a chain that can be assembled into three heterotrimers; a1/a1/a2, a3/a4/a5 and a5/a5/a6. The a1/a1/a2 and a3/a4/a5 heterotrimers are found in the GBM of the fetal and adult kidneys, respectively, while the a5/a5/a6 heterotrimer is found in the Bowman's capsule. Defects in any one of the three a chains in a heterotrimer impedes proper assembly and prevents deposition, of any of the proteins involved, into the GBM. The a3/a4/a5 heterotrimer is essential to the structure and function of the adult GBM, and, when absent, results in AS. Therefore, both XLAS and ARAS are characterized by the absence of COL4a3, COL4a4 and COL4a5 in the GBM of affected individuals.

While the underlying causes and modes of transmission of AS have been characterized, many aspects of the disease remain to be understood. As a result, the only treatment option is often renal transplant. Further investigation into this disease can be achieved through the use of available animal models. Therefore, it is clear that there is a need for a genetic test that permits the identification of animals with ARAS and carriers of ARAS.

It is therefore an object of the present invention to provide the mutation causative for ARAS in the dog.

It is a further object of the present invention to provide methods for detecting mutations in the COLa4 gene in dogs.

BRIEF SUMMARY OF THE INVENTION

Animals with mutations in COL4a4 present with autosomal recessive Alport Syndrome (ARAS). Through sequencing of COL4a4, the mutation causative for ARAS in the English Cocker Spaniel (ECS) has been identified. The resulting protein is severely truncated due to a premature stop codon in exon 3. This nonsense mutation occurs in the 7S domain and also causes the loss of the entire collagenous and NC1 domains of the protein. Methods for the identification of animals that harbor a mutation in the COL4a4 gene are described. Mutations in the COL4a4 gene can be identified from any biological sample such as a cell or tissue that contains genomic DNA. Methods for identifying single nucleotide polymorphisms (SNPs) that are inherited with the disease are also described. A microsatellite marker that segregates with ARAS is also described that was identified using linkage disequilibrium mapping.

DETAILED DESCRIPTION OF THE INVENTION

Definitions

Figure 1:
FIG. 1 is a diagram depicting the relative positions of COL4a3, COL4a4, FH3627, and FH3101, the microsatellite markers for which linkage disequilibrium (LD) was tested.
Figure 2A:
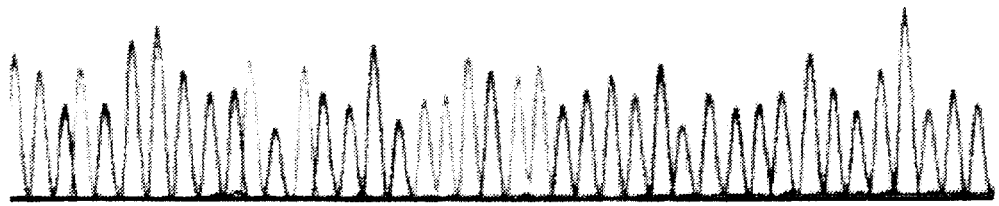
FIG. 2 is a chromatograph showing the nucleotide sequence for a) ARAS-unaffected ECS (SEQ ID No. 1), b) ARAS-carrier ECS (SEQ ID No. 1), and c) ARAS-affected ECS (SEQ ID No. 2). The asterisk indicates position of the single base change.
Figure 2B:
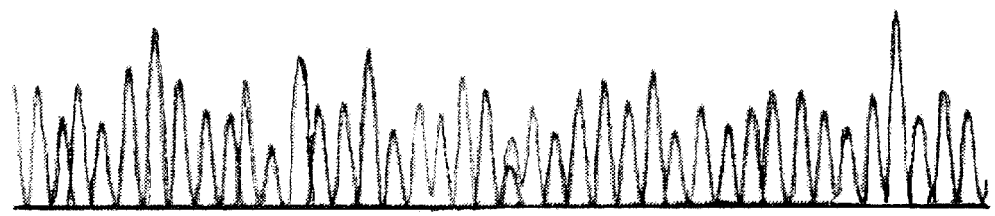
Figure 2C:
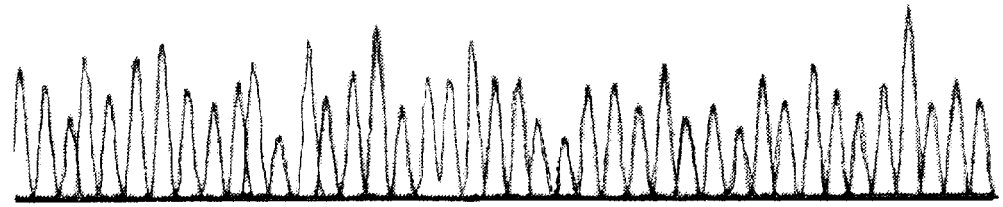

"Genetic marker" or "marker" as used herein refers to a variable or polymorphic nucleotide sequence that is present in genomic DNA, and which is identifiable with specific oligonucleotides (e.g., distinguishable by nucleic acid amplification and observance of a difference in size or sequence of nucleotides due to the polymorphism). The "locus" of a genetic marker or marker refers to its place on the chromosome in relation to another locus. Markers, as illustrated herein, can be identified by any one of several techniques know to those skilled in the art, including microsatellite or short tandem repeat (STR) amplification, analyses of restriction fragment length polymorphisms (RFLP), single nucleotide polymorphism (SNP), detection of deletion or insertion sites, and random amplified polymorphs DNA (RAPD) analysis.

"Co-segregate" as used herein refers to inheritance together of two specific loci; e.g., the loci are located so physically close on the same chromosome that the rate of genetic recombination between the loci is low, as observed by statistical analysis of inheritance patterns of alleles in a mating.

"Linkage" as used herein refers to co-segregation of two loci in the canine breed analyzed.

"Linkage test" and "molecular diagnostic assay" are terms used herein to refer to a method for determining the presence or absence of one or more allelic variants linked with a gene locus, such that the method may be used for the detection of mutant or carrier status, whether through statistical probability or by actual detection of a mutated gene.

"Polymorphism" as used herein refers to a marker that is distinguishably different (e.g., in size, electrophoretic migration, nucleotide sequence, ability to specifically hybridize to an oligonucleotide under standard conditions) as compared to an analogous region from an animal of the same type or pedigree (i.e., family tree).

"Nucleic acid amplification" or "amplify" as used herein refers to a process by which nucleic acid sequences are amplified in number. There are several means known to those skilled in the art for enzymatically amplifying nucleic acid sequences including polymerase chain reaction ("PCR"), ligase chain reaction (LCR), and nucleic acid sequence-based amplification (NASBA) as discussed in more detail below.

"Hybridization" as used herein refers to a sufficient number of complementary base pairs in its sequence to interact specifically (hybridize) with the target nucleic acid sequence to be amplified or detected. As known to those skilled in the art, a very high degree of complementarity is needed for specificity and sensitivity involving hybridization, although it need not be 100%. Thus, for example, an oligonucleotide which is identical in nucleotide sequence to an oligonucleotide disclosed herein, except for a few base changes or substitutions, may function equivalently to the disclosed oligonucleotides.

The COL4a4 Gene

Mouse and canine models for all three forms of AS (XLAS, ARAS and ADAS) are known. Included among these is the English Cocker Spaniel (ECS) breed of dog, in which an inherited form of renal disease, originally thought to be cortical hypoplasia, but now known to be ARAS, has been described for almost 50 years.

Previous work has suggested that the causative mutation for ARAS in the ECS is in the COL4a4 gene. However, the causative mutation has not been described. The gene expression patterns of COL4a4 mimic that of COL4a5 as described in more detail below, which harbors the mutation causative for XLAS in a mixed breed of dog. This data in conjunction with the LD data described below led to the subsequent sequence analysis of COL4a4, leading to the identification of the causative mutation in ARAS.

I. CAUSATIVE MUTATION OF ARAS AND MARKERS ASSOCIATED WITH ARAS

Although originally identified as cortical hypoplasia, hereditary renal disease (now known to be ARAS) has been described in ECS dogs for almost 50 years. This disease has had a devastating effect since the only treatment option for the disease (in any species) is renal transplantation, and until now, there was no way to identify carriers of the disease in order to avoid their breeding to another carrier. The elucidation of the cause of ARAS provides a means to identify carriers of the disease, which will provide a way for breeders to make educated decisions about matings to help eliminate AS from the breed.

It has previously been demonstrated that the form of AS which ECS dogs present with is transmitted as an autosomal recessive fashion (Lees, et al., *J. Vet. Intern. Med.* 11:80-85 (1997). The genetic cause for ARAS has been speculated to be mutations in either COL4a3 or COL4a4. As both of these genes are located in a head to head fashion on chromosome 25 in the canine, a test for linkage disequilibrium using two microsatellite markers on this chromosome was conducted. LD was identified for ARAS with marker FH3627, with a significant P value of 3.2e-7. FH3627 is the closest marker to COL4a4 (FIG. 1).

Sample Collection

DNA samples from ECS dogs from both the United States and Canada, were obtained from whole blood or buccal swab samples collected with the owners' consent. DNA was isolated from blood and buccal cells using the Puregene DNA Isolation Kit (Gentra Systems, Minneapolis, Minn.).

The dog's clinical status was determined to be either ARAS-affected, known carriers of ARAS, or status unknown. Diagnosis of ARAS-affected ECS dogs was made by pathologic, IF, and TEM evaluation as previously described (Lees, et al., *Kidney Int.* 54:706-719 (1998)). Sire and dam of ARAS-affected dogs were then determined to be known carriers of ARAS. All other dogs remained of unknown status.

LD Analysis

Linkage is the coinheritance of two or more nonallelic genes because their loci are in close proximity on the same chromosome, such that after meiosis they remain associated more often than the 50% expected for unlinked genes. During meiosis, there is a physical crossing over of genetic material, it is clear that during the production of germ cells there is a physical exchange of material and paternal genetic contributions between individual chromatids. This exchange necessarily separates genes in chromosomal regions that were contiguous in each parent and, by mixing them with retained linear order, results in "recombinants". The process of forming recombinants through meiotic crossing-over is an essential feature in the reassortment of genetic traits and is central to understanding the transmission of genes.

Recombination generally occurs between large segments of DNA. This means that contiguous stretches of DNA and genes are likely to be moved together. Conversely, regions of the DNA that are far apart on a given chromosome are more likely to become separated during the process of crossing-over than regions of the DNA that are close together.

The pattern of a set of markers along a chromosome is referred to as a "Haplotype". Therefore sets of alleles on the same small chromosomal segment tend to be transmitted as a block through a pedigree. By analyzing the haplotypes in a series of offspring of parents whose haplotypes are known, it is possible to establish which parental segment of which chromosome was transmitted to which child. When not broken up by recombination, haplotypes can be treated for mapping purposes as alleles at a single highly polymorphic locus.

The existence of a preferential occurrence of a disease gene in association with specific alleles of linked markers, such as single nucleotide polymorphisms (SNPs) or microsatellites, is called "Linkage Disequilibrium" (LD). This sort of disequilibrium generally implies that most chromosomes carry the same mutation and the markers being tested are very close to the gene carrying the mutation. By using a combination of several markers surrounding the presumptive location of the gene, a haplotype can be determined for affected and unaffected animals.

For any single gene disorder, identification of the defective gene can allow for screening of the at-risk population to identify carriers in an effort to reduce the frequency of the single gene disorder in that population. Linkage analysis is based on first finding the general chromosomal region in which the mutated gene is located, followed by identification of genetic markers to characterize a much smaller region of the chromosome containing the disease locus (the location of the mutated gene). The closer together the marker and the mutated gene are on the chromosome, the less likely a recombination event will occur between them during meioses; i.e., there is linkage between the marker and the mutated gene. The more closely linked the marker and mutated gene are, the more predictive and useful is the test for identifying carriers. Additionally, by using two or more marker loci, substantial additional information can be ascertained in a linkage analysis that can markedly increase the accuracy of the linkage test. For example, using multiple marker loci in a linkage analysis allows for the ability to screen various affected breeds of dogs to identify breed-specific haplotypes that characterize the COL4a4 allele in the specific breed of dog. Markers additional to those in the examples disclosed herein, the map either by linkage or by physical methods so close to the COL4a4 gene locus that any polymorphism in or with such derivative chromosomal regions, may be used in a molecular diagnostic assay for detection the carrier status of COL4a4.

A representative sample of dogs were analyzed for linkage disequilibrium using two microsatellite markers found on chromosome 25, the canine chromosome COL4a3 and COL4a4 are mapped to. These two markers, FH3627 and FH3101, are closest to the two genes of interest, flanking their head to head orientation, 1.3 Mb and 0.9 Mb away, respectively (FIG. 1) (Guyon, et al., *PNAS* 100:5296-5301 (2003)). Fifty-eight ECS dogs (11 ARAS-affected, 7 known carriers and 40 of unknown status) were genotyped for FH3627. Twenty-three ECS dogs (11 ARAS-affected, 9 known carriers, and 3 of unknown status) were genotyped for FH3101. Fisher's exact probability test for 2 X 2 tables was used to determine the P value of FH2327, the only marker with which an allele was associated with disease status. A P value of less than 0.0001 was considered significant (Hyun, et al., *Mamm. Genome* 14:640-649 (2003)).

Dogs were genotyped using fluorescently labeled primers for the two markers, designed from the 1 Mb canine Radiation Hybrid map (Guyon, et al., *PNAS* 100:5296-5301 (2003)). PCR was performed and products were resolved with an internal size standard (GeneScan 500 LIZ, Applied Biosystems, Foster City, Calif.) using an ABI 3100 DNA Analyzer (Applied Biosystems) and analyzed using GeneScan 3.1 (Applied Biosystems).

Sequencing of COL4a4

Forty-three sets of primers were designed to amplify complete exons and parts of the flanking introns using the published canine genome sequence (Table 1). Intron/exon boundaries were determined by aligning the canine genome sequence in the region on chromosome 25 around COL4a4 and the previously published mRNA sequence for COL4a4 (accession No. AY263363). One primer set was designed to amplify a region of cDNA containing two exons (Table 1).

TABLE 1

List of Primers Used to Amplify Exons of Col4a4.

| Exon | Sequence |
|---|---|
| 1 | F: CAGGGCATAGAACCTCACTTA (SEQ ID NO:3) |
|  | R: CTGCTGTGCTCTGGACATTAG (SEQ ID NO:5) |
| 2 | F: TCACTAATGACAGCAGCCTAT (SEQ ID NO:7) |
|  | R: ACCTGGGTAACTTGGTAAGAA (SEQ ID NO:9) |
| 3 | F: CCCTCTCACCAAGCCAC (SEQ ID NO:11) |
|  | R: GTTGCTGACTGTTGTTAGATGTT (SEQ ID NO:13) |
| 4 and 5ª | F: GGAGTGGAAAGAAGTTTGTCG (SEQ ID NO:15) |
|  | R: CCTCGTGAACCATTGTAGCC (SEQ ID NO:17) |
| 6 | F: GAGTCACCATTGCCATAACG (SEQ ID NO:19) |
|  | R: CAGCCTCCTCCCACAGTCT (SEQ ID NO:21) |
| 7 | F: GAAATCTCCACTAGCGAAAC (SEQ ID NO:23) |
|  | R: GCAAGAACAGTTAGGAGATACT (SEQ ID NO:25) |
| 8 | F: CCACACAGCCTTCCACAGTT (SEQ ID NO:27) |
|  | R: ACCCAGGTAATGCCAAATGAT (SEQ ID NO:29) |
| 9 | F: GATGTTTCTGGGACTGTGAT (SEQ ID NO:31) |
|  | R: ACTGGTAATGGGAGGTGTA (SEQ ID NO:33) |
| 10 and 11 | F: GAACCCAGGGCAACC (SEQ ID NO:35) |
|  | R: TTAACATCTGCTCCTCCAT (SEQ ID NO:37) |
| 12 | F: GCCACGCAGGATTGTATG (SEQ ID NO:39) |
|  | R: GCTGAGGTTGCTTTGGG (SEQ ID NO:41) |
| 13 and 14 | F: GAAGAGATAATGTCTGAAAGATGTA (SEQ ID NO:43) |
|  | R: CCCAGGTGCCCCAATA (SEQ ID NO:45) |
| 15 | F: GCCATAAAGCAGTTTCATAAG (SEQ ID NO:47) |
|  | R: ATCTGTAAAATAAATGTGTCTCC (SEQ ID NO:49) |
| 16 | F: ATGCGATACTGAGATTTTGC (SEQ ID NO:51) |
|  | R: GATACGAGGTGATCCCCA (SEQ ID NO:53) |
| 17 | F: GTCGGATTCCTTTGTCATTC (SEQ ID NO:55) |
|  | R: CCACCCAAGTCCCATCTC (SEQ ID NO:57) |
| 18 | F: CAGTGCTGCTCCAAGTTC (SEQ ID NO:59) |
|  | R: GGTGAGGGTGAGGCTGTC (SEQ ID NO:61) |
| 19 | F: CGGTTTCCATTTGTGTGC (SEQ ID NO:63) |
|  | R: CAGGCTTCATAGAACTGTTTG (SEQ ID NO:65) |
| 20 | F: CTTAGAGAGAAAGAGTCATAGGAA (SEQ ID NO:67) |
|  | R: AGGAGTGCTCATAGGCGTA (SEQ ID NO:69) |
| 21 | F: CCCCCCAACAGACCAT (SEQ ID NO:71) |
|  | R: CAGCACTGAGAACAGCACC (SEQ ID NO:73) |

TABLE 1-continued

List of Primers Used to Amplify Exons of Col4a4.

| Exon | Sequence |
|---|---|
| 22 | F: AGGTCAAGAGCCTCAGTTTTAT (SEQ ID NO:75) |
| | R: GAAATGTGAACAGCAAGGAATA (SEQ ID NO:77) |
| 23 | F: GTCCTGTGTTTCCTCCTACT (SEQ ID NO:79) |
| | R: CCAAAGATGGCTCTGATTA (SEQ ID NO:81) |
| 24 | F: GGTTTGCTATTGAGTAACTGTCTA (SEQ ID NO:83) |
| | R: TTATTGAACGGTTCTGCTGTA (SEQ ID NO:85) |
| 25 | F: AGGCAGTTCAAATCGTCTC (SEQ ID NO:87) |
| | R: AACTATTGGTTCATCATCTTAC (SEQ ID NO:88) |
| 26 | F: AGGCGAGGCAACAGTTACATA (SEQ ID NO:4) |
| | R: CCCTGGACCACCTGCTTAC (SEQ ID NO:6) |
| 27 | F: CAAGGTGGCAAAGCAAC (SEQ ID NO:8) |
| | R: GCATTCTACATTTCTAAGGC (SEQ ID NO:10) |
| 28 | F: CGTCGGTTGCTGGTACT (SEQ ID NO:12) |
| | R: GCTACTTGTCATTCTGTGGAG (SEQ ID NO:14) |
| 29 | F: GATGGATGTTGCTTCGTG (SEQ ID NO:16) |
| | R: GGATGGACAGTATCAGGCT (SEQ ID NO:18) |
| 30 | F: GTCCCACATCAGACTTCCT (SEQ ID NO:20) |
| | R: CTAAAGCAGACACCAGCAA (SEQ ID NO:22) |
| 31 | F: TACTGTGCTGATACTGTGCTG (SEQ ID NO:24) |
| | R: GCTGGAACTGGTATTAGATGT (SEQ ID NO:26) |
| 32 | F: TATGGCTTAGGGCAGGAA (SEQ ID NO:28) |
| | R: AAGGGCAATGATGTTTACAGA (SEQ ID NO:30) |
| 33 | F: CACCTCTAATACTGGAGTTGTA (SEQ ID NO:30) |
| | R: ATGCTAAATGTGCGTGCT (SEQ ID NO:34) |
| 34 | F: TGAAGATAAACTATAAAGACAAAT (SEQ ID NO:36) |
| | R: TGGAGCCCAACACAAG (SEQ ID NO:38) |
| 35 | F: CAAGGGCTGAAGTTGGAGGTT (SEQ ID NO:40) |
| | R: GAGGGATGGGTAGGTCTGAGTG (SEQ ID NO:42) |
| 36 | F: AGGTCTAGGGGATAAAAGTG (SEQ ID NO:44) |
| | R: CTGAGTGAGAGAGAAGAGGAA (SEQ ID NO:46) |
| 37 | F: GAGCGTGTTAAATAATAGCCA (SEQ ID NO:48) |
| | R: TCATCTTCAGTCCTAATAATAGTCC (SEQ ID NO:50) |
| 38 and 39 | F: GCAGCAGGTGGTTGGTCTCAGCA (SEQ ID NO:52) |
| | R: CCACCTGCCGCATTGA (SEQ ID NO:54) |
| 40 | F: CCCTTCATCTCTCGCTTGC (SEQ ID NO:56) |
| | R: GAACTTGTGTTTCTTCCCCTTAC (SEQ ID NO:58) |

TABLE 1-continued

List of Primers Used to Amplify Exons of Col4a4.

| Exon | Sequence |
|---|---|
| 41 | F: TGGGTTCAGTCCATCAGA (SEQ ID NO:60) |
| | R: GAATAGGGTCCTCACATACAG (SEQ ID NO:62) |
| 42 | F: GGATGGGGACTTAGTTATGTA (SEQ ID NO:64) |
| | R: AAGCACTCACGCTCTGG (SEQ ID NO:66) |
| 43 | F: GGACTGTTGAGCATTCTTTG (SEQ ID NO:68) |
| | R: GCTTACACTGCCCCATACT (SEQ ID NO:70) |
| 44 | F: CTCGGGCTCAGGGTCTAAC (SEQ ID NO:72) |
| | R: GGCTGCGGATCAGTGC (SEQ ID NO:74) |
| 45 | F: CTCCTCCTCTCTGGCTCC (SEQ ID NO:76) |
| | R: TAAAATGTTGATGAATCTGTAAAAT (SEQ ID NO:78) |
| 46 | F: GGAGGCGTGTCTGTGGGT (SEQ ID NO:80) |
| | R: CCGTGTCTCAAGAGGCTATGG (SEQ ID NO:82) |
| 47 | F: GTTGGTTCTTCCCTGGATAAT (SEQ ID NO:84) |
| | R: AACTGGAGTCTGAAATGAGCAC (SEQ ID NO:86) |

Reverse transcription was performed to generate cDNA using the Enhanced Avian First Strand Synthesis Kit (Sigma-Aldrich Co., St. Louis, Mo.). Amplification by PCR was conducted with each reaction containing 50 ng of DNA, 2 mM of MgCl, 0.25 mM of each dNTP, 1.0 uM of each primer (forward and reverse), 5% DMSO, 0.001 mg of Bovine Serum Albumin (Promega, Madison, Wis.) 0.75 units of Taq DNA Polymerase (Fisher Scientific, Pittsburgh, Pa.) 1 ul of 1 X Taq DNA Polymerase Buffer B (Fisher Scientific). Amplification cycling conditions were as follows 94° C. for 5 minutes, followed by 35 cycles of 94° C. for 30 seconds, 55°-58° C. for 30 seconds and 72° C. for 30 seconds, then a single cycle at 72° C. for 10 minutes. Amplified DNA products were separated by gel electrophoresis and then visualized using ethidium bromide. When multiple amplification products were present, the desired amplicon was purified using the Qiaex® II Gel Extract Kit (Qiagen, Inc., Valencia, Calif.). If only the desired amplicon was present, 7 ul of the amplified DNA product was purified using 10 units of Exonuclease I (Eppicentre, Madison, Wis.) and 1 unit of Shrimp Alkaline Phosphatase (Roche, Indianapolis, Ind.) and incubated at 37° C. for 30 minutes and then at 80° C. for 15 minutes. Purified products were then used for nucleotide sequencing reactions using the Big Dye Terminator v 1.1. Cycle Sequencing Kit (Applied Biosystems) and resolved on an ABI 3730 Genetic Analyzer (Applied Biosystems). Sequence was obtained from 2 ARAS-affected ECS dogs, 2 known carriers of ARAS, 2 ECS dogs of unknown status, and 2 ARAS-unaffected dogs of mixed breed origin. To verify the mutation, exon 3 was amplified and sequenced from 12 ARAS-affected ECS dogs, 8 known carrier ECS dogs and 114 ECS of unknown status. Sequences were aligned using Clustal W (http://www.ebi.ac.uk/clustalw/) and nucleotide discrepancies which segregate with AS-affected ECS dogs were identified.

In order to capture both coding regions and splice sites, primers were designed within flanking introns such that the 47 exons of the gene and surrounding intronic sequences were amplified and sequenced separately (with the exception of six exons which could be sequenced together due to the short length of the connecting intron and two exons which were sequenced from cDNA) (Table 1). This allowed for analysis of the entire coding region as well as intron/exon splice sites. Sequence analysis revealed a single nucleotide substitution at base 115 (A to T), causing a nonsense mutation in codon 39 (lysine to stop). While verifying the mutation 114 ECS dogs of unknown status were sequenced, of these 43 were shown to be heterozygous for the causative allele, and 71 were shown to be homozygous for the unmutated allele. This gave a total of 12 ARAS-affected ECS dogs, 51 ECS dog carriers of ARAS, and 71 normal ECS dogs which were tested for the causative mutation. For every ARAS-affected ECS dog sequenced, base 115 was a T, while all known carriers sequenced had both an A and T at base 115. This sequence was compared to both the published canine coding sequence for COL4a4 (accession AY263363), and the published 7X NIH genomic reference sequence for the canine. Both have an A at base 115.

Also segregating with the disease and two single nucleotide polymorphisms (SNPs) A T to A substitution 93 bases upstream of exon 42 and a T to C substitution 90 bases upstream of exon 42. Neither of these polymorphisms change the coding sequence of the gene but both are inherited with the disease.

One SNP which is linked to the disease but does not segregate 100% (7 out of 134 do not segregate) was also identified. This SNP (a T to C substitution) is 32 bases upstream of exon 3 and 41 bases upstream of the mutation in exon 3. The sequence surrounding the SNP that segregates with the normal allele can be cut with BsrI. However, the sequence surrounding the SNP that segregates with the affected allele can not be cut by BsrI but instead by AgeI and Cfr10I. Again, this SNP is located in the intron and therefore does not change the coding sequence.

A SNP which segregates with affected dogs along with these SNP was identified. However, two alleles in a known carrier were not observed using direct sequencing. Two alleles for an unknown, but suspected carrier ECS dog, were observed, however. This change occurs at coding position 4,602 and changes a G to an A. This nucleotide change does not change an amino acid, but does occur in affected ECS, and not in an unaffected published Dalmation sequence (accession NO. AY263363), NIH reference sequence from the Boxer, or a mixed breed kindred sequenced for this study.

Allele Frequency

Once a causative mutation was determined, the frequency of the allele harboring this mutation was established. DNA from 134 ECS was amplified using the primers described for exon 3 (Table 1), and the nucleotide sequence determined as described.

In order to assess the frequency of this allele, sequence from the aforementioned 134 ECS dogs were examined for the presence of the stop codon. The group represented at least four kindred, and were shown to contain 12 ARAS-affected, 51 ARAS-carrier, and 71 ARAS-unaffected dogs. Therefore, 193 alleles were not mutated, and 75 alleles harbored the mutation. Thus, the frequency of the allele containing the premature stop codon causative for ARAS in the ECS, for the group as a whole is 0.27985. However, two of the four kindred, with sizes of 19 and 6 dogs, did not contain affected dogs and have the following allele frequencies: 0.0789 and 0, respectively.

II. METHODS FOR TESTING

Samples

Samples are obtained from an animal to be tested using standard techniques and reagents. In a preferred embodiment, the biological sample is any tissue containing genomic DNA. Most preferably, the biological sample is blood, hair follicles, mucosal scrapings, semen, tissue biopsy, or saliva. In the most preferred embodiment, the biological sample is blood.

Methods of screening a biological sample for mutated nucleic acids can be carried out using either deoxyribonucleic acids ("DNA") or messenger ribonucleic acids ("mRNA") isolated from the biological sample. During periods when the gene is expressed, mRNA may be abundant and more readily detected. However, these genes are temporally controlled and, at most stages of development, the preferred material for screening is DNA.

Methods For Screening

Methods of using genetic markers, such as SNPs and microsatellite markers, for determining whether an animal has a mutated COL4a4 gene locus in one or both alleles and methods for identification of animals that harbor a mutation in the COL4a4 gene are described herein.

The reagents typically consist of oligonucleotides that identify either the:

(1) mutation in the COL4a4 gene; or
(2) the microsatellite marker associated with the mutation in the COL4a4 gene; and/or,
(3) polymorphisms associated with the mutation in the COL4a4 gene.

In the preferred embodiment the reagents identify the base substitution at base 115 in exon 3 of the COL4a4 gene that results in a premature stop codon, the microsatellite marker FH3627 and/or a polymorphism. Preferably the polymorphism is a T to A base substitution 93 bases upstream of exon 42, a T to C base substitution 90 bases upstream of exon 42 and/or a T to C base substitution 32 bases upstream of exon 3.

The nucleic acid and protein sequence for the COL4a4 gene can be found at http://www.ncbi.nlm.nih.gov/ accession number AY263363.

The sequence surrounding the mutation in unaffected ECS is:

ACTAAACCAGATGCTTCACTTTCCAGAGTGGAA AG[A]AGTTTGTCGGC CCCTGTGGAGGAAGAGAT-TGCTCG (SEQ ID NO:89).

The sequence surrounding the mutation in affected ECS is:

ACTAAACCAGATGCTTCACTTTCCAGAGTGGAA AG[T]AGTTTGTCGGC CCCTGTGGAGGAAGAGAT-TGCTCG (SEQ ID NO:90).

The sequence surrounding SNPs 93 and 90 bases upstream of exon 42 in unaffected ECS is:

CCTCAAAGTATTATGTATAATTCTCGAATAACC GA[T]TT[T]GCTTTTGCC CTAACTGACAAATT-TAAAATCTCTTT (SEQ ID NO:91).

The sequence surrounding SNPs 93 and 90 bases upstream of exon 42 in affected ECS is:

CCTCAAAGTATTATGTATAATTCTCGAATAACC GA[A]TT[C]GCTTTTGCC CTAACTGACAAATT-TAAAATCTCTTT (SEQ ID NO:92).

The sequence surrounding SNP 32 bases upstream of exon 3 in unaffected ECS is:

TGTACACATCATGTGCCCAGCTCAGTGTGCAAT AC[T]GGTTTACTAAA CCAGATGCTTCACTTTCCA-GAGTG (SEQ ID NO:93).

The sequence surrounding SNP 32 bases upstream of exon 3 in affected ECS is:

TGTACACATCATGTGCCCAGCTCAGTGTGCAAT AC[C]GGTTTACTAAA CCAGATGCTTCACTTTCCA-GAGTG (SEQ ID NO:94).

The base(s) in bold font and in a box in the aforementioned sequences indicate mutation or SNP site.

The nucleic acid molecules may be linked to other nucleic acid molecules such as vectors or tags to facilitate amplification, purification, or identification. These may be used in any of the following assays or others used by those skilled in the art for genetic analysis.

The COL4a4 gene can be screened for any type of mutation by numerous methods well known to one of ordinary skill in the art. Nucleotide sequencing can be used to test for the presence of an allele harboring the mutation; however, other methods may be employed to test for mutated alleles. These methods include, but are not limited to, enzymatic cleavage at the restriction sites surrounding the SNPs mentioned below, heteroduplex identification as described in White, et al., *Genomics* 12:301-306 (1992) for example, allele specific oligonucleotide (ASO) probes (e.g., Saiki, et al., *Nature* 324:163-166 (1986)), a colorimetric oligo-ligation assay (OLA) (e.g., Delahunty, et al., *Am. J. Hum. Genet.* 58:1239-1246 (1996)), solid-phase minisequencing (e.g., Syvanen, et al., *Genomics* 12:590-595 (1992)), single strand conformation polymorphisms (SSCP) (e.g., Orita, et al., *PNAS* 2766-2770 (2989)), dideoxy fingerprinting (ddE) (e.g., Sarkar, et al., *Genomics* 13:441-443 (1992)), high-performance liquid chromatography (HPLC) or denaturing HPLC (D-HPLC) (e.g., O'Donovan, et al., *Genomics* 52:44-49 (1998)), stem-loop cleavage fragment length polymorphisms using enzymes such as Cleavease (e.g., Marshall, et al., *Clin. Microbiol.* 35:3156-3162 (1997)), ribonuclease cleavage (e.g., Myers, et al., *Science* 230:1242-1246 (1985)), and DNA endonuclease cleavage of heteroduplexes (e.g., Mashal, et al., *Nature Genet.* 9:177-183 (1995)).

In a preferred embodiment, the method for determining the genotype of an animal as it applies to the COL4a4 gene is a PCR-based test followed by gel electrophoresis or DNA sequencing. For example, DNA is extracted from check swabs taken from dogs or humans. The DNA is amplified by PCR using primers that hybridize to the COL4a4 gene, preferably primers that amplify exon 3 of the COL4a4 gene (see Table 1). The resulting amplified DNA fragments can be sequenced to identify the mutation in the COL4a4 gene.

Other approaches to reveal the presence of the mutation in the COL4a4 gene include, but are not limited to, Southern blotting using probes to the region of interest; fluorescently labeled primers that amplify the region of interest which is then analyzed using automated technology; different primers that bracket the region of interest.

Oligonucleotide Ligation Assay ("OLA") (Landegren et al., "A Ligase-Mediated Gene Detection Technique," Science, 241:1077-1080 (1988); Landegren et al., "DNA Diagnostics—Molecular Techniques and Automation," Science, 242:229-237 (1988); U.S. Pat. No. 4,988,617 to Landegren et al.), is one method for testing the genetic material in the biological sample. The OLA protocol uses two oligonucleotides which are designed to be capable of hybridizing to abutting sequences of a single strand of a target. One of the oligonucleotides is biotinylated, and the other detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. OLA is capable of detecting insertion mutations. However, numerous methods for characterizing or detecting mutations are known in the art and any of those methods are also suitable.

Another method of characterizing a mutation entails direct DNA sequencing of the genetic locus that flanks and includes the insertion. Such analysis can be accomplished using either the "dideoxy-mediated chain termination method," also known as the "Sanger Method" (Sanger et al., "DNA Sequencing with Chain-Terminating Inhibitors," Proc. Natl. Acad. Sci. USA, 74:5463-5467 (1977)) or the "chemical degradation method," also known as the "Maxam-Gilbert method" (Maxam et al., "A New Method for Sequencing DNA," Proc. Natl. Acad. Sci. USA, 74:560-564 (1977)).

One example of a procedure for sequencing DNA molecules using arrays of oligonucleotides is disclosed in U.S. Pat. No. 5,202,231 to Drmanac et al. This involves application of target DNA to a solid support to which a plurality of oligonucleotides are attached. Sequences are read by hybridization of segments of the target DNA to the oligonucleotides and assembly of overlapping segments of hybridized oligonucleotides. The array utilizes all possible oligonucleotides of a certain length between 11 and 20 nucleotides, but there is little information about how this array is constructed. See also Chetverin et al., "Sequencing of Pools of Nucleic Acids on Oligonucleotide Arrays," BioSystems 30:215-31 (1993): WO 92/16655 to Khrapko et al.; Kuznetsova et al., "DNA Sequencing by Hybridization with Oligonucleotides Immobilized in Gel. Chemical Ligation as a Method of Expanding the Prospects for the Method," Mol. Biol. 28(20): 290-99(1994); Livits et al., "Dissociation of Duplexes Formed by Hybridization of DNA with Gel-Immobilized Oligonucleotides," J. Biomolec. Struct. & Dynam. 11(4): 783-812 (1994).

WO 89/10977 to Southern, discloses the use of a support carrying an array of oligonucleotides capable of undergoing a hybridization reaction for use in analyzing a nucleic acid sample for known point mutations, genomic fingerprinting, linkage analysis, and sequence determination. The matrix is formed by laying nucleotide bases in a selected pattern on the support. This reference indicates that a hydroxyl linker group can be applied to the support with the oligonucleotides being assembled by a pen plotter or by masking.

Single strand polymorphism assay ("SSPA") analysis and the closely related heteroduplex analysis methods are methods for screening for single-base mutations (Orita et al., "Detection of Polymorphisms of Human DNA by Gel Electrophoresis as Single-Strand Conformation Polymorphisms," Proc. Natl. Acad. Sci. USA, 86:2766-2770 (1989)). In these methods, the mobility of PCR-amplified test DNA from clinical specimens is compared with the mobility of DNA amplified from normal sources by direct electrophoresis of samples in adjacent lanes of native polyacrylamide or other types of matrix gels. Single-base changes often alter the secondary structure of the molecule sufficiently to cause slight mobility differences between the normal and mutant PCR products after prolonged electrophoresis.

Ligase chain reaction is another method of screening for mutated nucleic acids (see Barany, "Genetic Disease Detection and DNA Amplification Using Cloned Thermostable Ligase," Proc. Natl. Acad. Sci. USA, 88:189-193 (1991); Barany, "The Ligase Chain Reaction (LCR) in a PCR World," PCR Methods and Applications, 1:5-16 (1991); WO 90/17239 to Barany et al.; Barany et al., "Cloning, Overexpression and Nucleotide Sequence of a Thermostable DNA Ligase-Encoding Gene," Gene, 109:1-11 (1991); and Barany, "Genetic Disease Detection and DNA Amplification Using Cloned Thermostable Ligase," Proc. Natl. Acad. Sci. USA, 88:189-193 (1991). In general, the LCR procedure is carried out with two pairs of oligonucleotide probes: one pair binds to one strand of the target sequence to be detected; the other pair binds to the other complementary strand of the target sequence to be detected. The reaction is carried out by denaturing the strands of the target sequence, then reacting the separated strands with the two pairs of oligonucleotide probes in the presence of a heat stable ligase so that each pair of oligonucleotide probes hybridizes to target DNA and, if there is perfect complementarity at their junction, adjacent probes are ligated together. If such complementarity is lacking, no ligation occurs and the probes separate individually from the target sequence during denaturation. The ligated or unligated probes are then separated during the denaturation step. The process is cyclically repeated until the sequence has been amplified to the desired degree. Detection can then be carried out by electrophoresis or by capture hybridization or an array of DNA probes. Ligated and unligated probes can then be detected to identify the presence of a mutation.

The ligase detection reaction (LDR) process is another method for detecting a mutation described generally in WO 90/17239 to Barany et al., Barany et al., "Cloning, Overexpression and Nucleotide Sequence of a Thermostable DNA Ligase-encoding Gene," Gene, 109:1-11 (1991), and Barany, "Genetic Disease Detection and DNA Amplification Using Cloned Thermostable Ligase," Proc. Natl. Acad. Sci. USA, 88:189-193 (1991). The ligase detection reaction is similar to the LCR technique; however, in LDR, there is only one pair of oligonucleotide probes which are complementary to one strand of the target sequence. While LCR provides an opportunity for exponential amplification, LDR achieves linear amplification.

Mundy et al. (U.S. Pat. No. 4,656,127) discusses alternative methods for determining the identity of the nucleotide present at a particular polymorphic site. Nundy's methods employ a specialized exonuclease-resistant nucleotide derivative. A primer complementary to the allelic sequence immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonuclease reveals that the nucleotide present in the polymorphic site of the target molecule was complementary to that of the nucleotide derivative used in the reaction.

Several primer-guided nucleotide incorporation procedures, for assaying polymorphic sites (i.e., sites of mutations) in DNA have been described (Kornher et al., "Mutation Detection Using Nucleotide Analogs that Alter Electrophoretic Mobility," Nucl. Acids. Res., 17:7779-7784 (1989); Sokolov, "Primer Extension Technique for the Detection of Single Nucleotide in Genomic DNA," Nucl. Acids Res., 18:3671 (1990); Syvanen et al., "A Primer-Guided Nucleotide Incorporation Assay in the Genotyping of Apolipoprotein E," Genomics, 8:684-692 (1990); Kuppuswamy et al., "Single Nucleotide Primer Extension to Detect Genetic Diseases: Experimental Application to Hemophilia B (Factor IX) and Cystic Fibrosis Genes," Proc. Natl. Acad. Sci. USA, 88:1143-1147 (1991); Prezant et al., "Trapped-Oligonucleotide Nucleotide Incorporation (TONI) Assay, a Simple Method for Screening Point Mutations," Hum. Mutat., 1:159-164 (1992); Ugozzoli et al., "Detection of Specific Alleles by Using Allele-specific Primer Extension Followed by Capture on Solid Support," GATA, 9:107-112 (1992); Nyren et al., "Solid Phase DNA Minisequencing by an Enzymatic Luminometric Inorganic Pyrophosphate Detection Assay," Anal. Biochem., 208:171-175 (1993). These methods differ from Genetic Bit Analysis™ ("GBA™" discussed extensively below) in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen et al., "Identification of Individuals by Analysis of Biallelic DNA Markers, Using PCR and Solid-Phase Minisequencing," Amer. J. Hum. Genet., 52:46-59 (1993)).

Cohen et al. (French Patent 2,650,840; PCT Application No. WO 91/02087, discuss a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nucleotide of that site using labeled dideoxynucleotide derivatives, which, if complementary to the nucleotide of the polymorphic site, will become incorporated onto the temrinus of the primer.

An alternative method, known as Genetic Bit Analysis™ or GBA™ is described by Goelet et al. PCT Publication No. WO 92/15712. In a preferred embodiment, the method of Goelet et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. French Patent 2,650,840; PCT Publication No. WO 91/02087, the method of Goelet et al. is preferably a heterogeneous phase assay, in which the primer or the target molecule is immobilized to a solid phase.

Other methods for detecting the presence of mutations include: differential restriction endonuclease digestion (DRED), allele-specific oligonucleotide probing (ASOP), and ligase-mediated gene detection (LMGD). Additional methods of analysis could also be useful in this context, such as fluorescence resonance energy transfer (FRET) as disclosed by Wolf et al., "Detection of Nucleic Acid Hybridization by Nonradiative Fluorescence Resonance Energy Transfer," Proc. Nat. Acad. Sci. USA, 85: 8790-94 (1988).

DRED analysis is accomplished in the following manner. If conditions occur including (1) a particular amplified cDNA segment contains a sequence variation that distinguishes an allele of a polymorphism and (2) this sequence variation is recognized by a restriction endonuclease, then the cleavage by the enzyme of a particular polynucleotide segment can be used to determine the alloantigen phenotype. In accomplishing this determination, amplified cDNA derived from platelet or red blood cell mRNA is digested and the resulting fragments are analyzed by size. The presence or absence of nucleotide fragments, corresponding to the endonuclease-cleaved fragments, determines which phenotype is present.

In ASOP analysis according to conventional methods, oligonucleotide probes are synthesized that will hybridize, under appropriate annealing conditions, exclusively to a particular amplified cDNA segment that contains a nucleotide sequence that distinguishes one allele from other alleles of a red blood cell or platelet membrane glycoprotein. This specific probe is discernibly labeled so that when it hybridizes to the allele distinguishing cDNA segment, it can be detected, and the specific allele is thus identified.

In LMGD, as disclosed by Landegren et al., "Ligase-Mediated Gene Detection Technique," Science, 241: 1077-80 (1988), a pair of oligonucleotide probes are synthesized that will hybridize adjacently to each other, i.e., to a cDNA segment under appropriate annealing conditions, at the specific nucleotide that distinguishes one allele from other alleles. Each of the pair of specific probes is labeled in a different manner, and when it hybridizes to the allele-distinguishing cDNA segment, both probes can be ligated together by the addition of a ligase. When the ligated probes are isolated from the cDNA segments, both types of labeling can be observed together, confirming the presence of the allele-specific nucleotide sequence. Where the above-described pair of differently labeled probes bind to a nucleotide sequence containing a distinguishing nucleotide of a different allele, the probe pair is not ligatable and, after the probes are isolated from the cDNA segments, both types of labeling are observed separately.

WO 94/11530 to Cantor, relates to the use of an oligonucleotide array to carry out a process of sequencing by hybridization. The oligonucleotides are duplexes having overhanging ends to which target nucleic acids bind and are then ligated to the non-overhanging portion of the duplex. The array is constructed by using streptavidin-coated filter paper which captures biotinylated oligonucleotides assembled before attachment.

WO 93/17126 to Chetverin, uses sectioned, binary oligonucleotide arrays to sort and survey nucleic acids. These arrays have a constant nucleotide sequence attached to an adjacent variable nucleotide sequence, both bound to a solid support by a covalent linking moiety. The constant nucleotide sequence has a priming region to permit amplification by PCR of hybridized strands. Sorting is then carried out by hybridization to the variable region. Sequencing, isolating, sorting, and manipulating fragmented nucleic acids on these binary arrays are also disclosed. In one embodiment with enhanced sensitivity, the immobilized oligonucleotide has a shorter complementary region hybridized to it, leaving part of the oligonucleotide uncovered. The array is then subjected to hybridization conditions so that a complementary nucleic acid anneals to the immobilized oligonucleotide. DNA ligase is then used to join the shorter complementary region and the complementary nucleic acid on the array.

WO 92/10588 to Fodor et al., discloses a process for sequencing, fingerprinting, and mapping nucleic acids by hybridization to an array of oligonucleotides. The array of oligonucleotides is prepared by a very large scale immobilized polymer synthesis which permits the synthesis of large, different oligonucleotides. In this procedure, the substrate surface is functionalized and provided with a linker group by which oligonucleotides are assembled on the substrate. The regions where oligonucleotides are attached have protective groups (on the substrate or individual nucleotide subunits) which are selectively activated. Generally, this involves imaging the array with light using a mask of varying configuration so that areas exposed are deprotected. Areas which have been deprotected undergo a chemical reaction with a protected nucleotide to extend the oligonucleotide sequence where imaged. A binary masking strategy can be used to build two or more arrays at a given time. Detection involves positional localization of the region where hybridization has taken place. See also U.S. Pat. Nos. 5,324,633 and 5,424,186 to Fodor et al., U.S. Pat. Nos. 5,143,854 and 5,405,783 to Pirrung et al., WO 90/15070 to Pirrung et al., Pease et al., "Light-generated Oligonucleotide Arrays for Rapid DNA Sequence Analysis", Proc. Natl. Acad. Sci USA 91:5022-26 (1994), which are hereby incorporated by reference. Beattie et al., "Advances in Genosensor Research," Clin. Chem. 41(5): 700-09 (1995), discloses attachment of previously assembled oligonucleotide probes to a solid support.

Landegren et al., "Reading Bits of Genetic Information: Methods for Single-Nucleotide Polymorphism Analysis," Genome Research, 8:769-776 (1998), discloses a review of methods for mutation analysis.

In another embodiment, testing the biological sample includes amplifying a region of the COLa4 gene to provide an amplified fragment before detecting any mutation present in the biological sample.

Amplification of a selected, or target, nucleic acid sequence may be carried out by any suitable means, either to facilitate sequencing or for direct detection of mutations. (See generally Kwoh et al., "Target Amplification Systems in Nucleic Acid-Based Diagnostic Approaches," Am. Biotechnol. Lab., 8:14-25 (1990)). Examples of suitable amplification techniques include, but are not limited to, polymerase chain reaction, ligase chain reaction ("LCR") strand displacement amplification (see generally, Walker et al., "Strand Displacement Amplification—An Isothermal, In Vitro DNA Amplification Technique," Nucleic Acids Res., 20:1691-1696 (1992); Walker et al., "Isothermal In-Vitro Amplification of DNA By a Restriction Enzyme-DNA Polymerase System," Proc. Natl. Acad. Sci. USA 89:392-396 (1992), transcription-based amplification (see Kwoh et al., "Transcription-Based Amplification System and Detection of Amplified Human Immunodeficiency Virus Type 1 With a Bead-Based Sandwich Hybridization Format," Proc. Natl. Acad. Sci. USA 86:1173-1177 (1989), self-sustained sequence replication (or "3SR") (see Guatelli et al., "Isothermal In-Vitro Amplification of Nucleic Acids By a Multienzyme Reaction Modeled After Retroviral Replication," Proc. Natl. Acad. Sci. USA 87:1874-1878 (1990), the Qβ replicase system (see Lizardi et al., "Exponential Amplification of Recombinant RNA Hybridization Probes," Biotechnology, 6:1197-1202 (1988), nucleic acid sequence-based amplification (or "NASBA"), the repair chain reaction (or "RCR"), and boomerang DNA amplification (or "BDA") (see Lewis, "Review of Progress in Developing Amplification Technologies Which May Compete With Roche Diagnostic Systems" Polymerase Chain Reaction (PCR)," Genetic Engineering News, 12(9):1, 8-9 (1992)). Polymerase chain reaction is currently preferred.

Genomic sequence-specific amplification technologies, such as the polymerase chain reaction (Mullis et al., "Specific Enzymatic Amplification of DNA in Vitro the Polymerase Chain Reaction," Cold Spring Harbor Symp. Quant. Biol. 51:263-274 (1986); European Patent Application No. 50,424 to Erlich et al.; European Patent Application No. 84,796 to Erlich et al.; European Patent Application 258,017 to Erlich et al.; European Patent Application No. 237,362 to Erlich et al.; European Patent Application No. 201,184 to Mullis; U.S. Pat. No. 4,683,202 to Mullis et al.; U.S. Pat. No. 4,582,788 to Erlich; Saiki et al., "Enzymatic Amplification of Beta Globin Genomic Sequences and Restriction Site Analysis for Diagnosis of Sickle Cell Anemia," Science 230:1350-1354 (1985); and U.S. Pat. No. 4,683,194 to Saiki et al.), may be employed to facilitate the recovery of the desired polynucleotides. In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

Testing the biological sample includes performing PCR using genomic DNA templates. In particular, PCR is performed using primers spanning the location of the mutation. In one embodiment, the testing of the genetic material in the biological sample is carried out by Taq cycle sequencing. The method for cycle sequencing, based on linear amplification of template DNA by polymerase chain reaction, was described by Murray, "Improved Double Stranded Sequencing Using the Linear Polymerase Chain Reaction," Nucleic Acids Research, 17:88-89 (1989). This technique essentially combines thermocycling procedure using Taq polymerase with dideoxy sequencing. In principle, the sequencing reaction consists of primer annealing to the template DNA followed by repeated extension of the primer by Taq polymerase in the presence of dNTPs/ddNTPs, linearly amplifying the sequence reaction products. Currently, cycle sequencing is done almost exclusively by non-isotopic methods using an automated DNA sequencer. A popular format for the sequencing protocol developed by Probe et al., "A System for Rapid DNA Sequencing with Fluorescent Chain-Terminating Dideoxynucleotides," Science, 238:336-341 (1987), is based on the use of a set of four chain-terminating dideoxynucleotides, each coupled to a different fluorescent dye and distinguishable by fluorescence emission. The DNA fragments are resolved by gel electrophoresis in one sequencing lane and detected by a scanning fluorescence detection system with computer-based automatic sequence identification.

One method that can be used to detect a mutation is polymerase chain reaction restriction fragment length polymorphism (PCR-RFLP). Single nucleotide changes in the genes are common phenomenon. Such alterations, depending on their locations, can be innocuous or deleterious to the gene function. Single base changes can alter the recognition sequence of restriction enzymes resulting in creation of a new, or abolition of an existing, restriction site, giving rise to variation in DNA fragment length. The variants are called restriction fragment length polymorphism (RFLP). These are inherited in a codominant fashion and are allelic variants, generating homozygous and heterozygous genotypes. Identification of RFLP in mammalian genome has been classically determined by Southern blot analysis. Use of polymerase chain reaction (PCR) to detect RFLP has dramatically accelerated the pace of initial identification and subsequent assaying of a large number of samples in an easy to use format. In short, two oligonucleotide primers are designed from the region of the genome flanking the suspected variation in the sequence between two alleles. These primer pairs are used to amplify the encompassing region of interest from genomic DNA by PCR using Taq polymerase and dNTPs in the presence of an optimal concentration of magnesium chloride. The PCR products are digested with the restriction enzyme with altered recognition sites between two alleles of the genome, and the digested DNA fragments are separated by electrophoresis in a solid matrix of choice (e.g., agarose or polyacrylamide) depending on the size of the fragments. (See, e.g., Ray et al., "Molecular Diagnostic Test for Ascertainment of Genotype at the Rod Cone Dysplasia (red1) Locus in Irish Setters," Current Eye Research, 14:243-247 (1995); Ray et al., "A Highly Polymorphic RFLP Marker in the Canine Transducin .alpha.-1 Subunit Gene," Animal Genetics, 27:372-373 (1996); Ray et al., "PCR/RFLP Marker in the Canine Opsin Gene," Animal Genetics, 27:293-294 (1996); Wang et al., "PCR/RFLP Marker in the Canine Transducin-gamma. Gene (GNGT1)," Animal Genetics, 28:319-320 (1997); Gu et al., "Detection of Single Nucleotide Polymorphism," BioTechniques, 24:836-837 (1998) and Zeiss et al., "A Highly Polymorphic RFLP Marker in the Canine Retinitis Pigmentosa (GTPase Regulator (RPGR) Gene," Animal Genetics, 29:409 (1998), which are hereby incorporated by reference). In addition to the rapidity of the PCR-RFLP technique, it also offers the flexibility to create an allele specific restriction site when the nucleotide change does not naturally create a RFLP. This is routinely done by deliberately incorporating a mismatch nucleotide in one of the primers such that a restriction site is created in one of the two alleles.

Nickerson et al. have described a nucleic acid detection assay that combines attributes of PCR and OLA (Nickerson et al., "Automated DNA Diagnostics Using an Elisa-Based Oligonucleotide Ligation Assay," Proc. Natl. Acad. Sci. USA, 87:8923-8927 (1990)). In this method, PCR is used to achieve the exponential amplification of target DNA, which is then detected using OLA.

Methods for Screening for the Analogous Gene in Humans

Alport Syndrome (AS) is hereditary progressive glomerular nephritis caused by mutations in the genes that encode certain proteins in the type IV collagen family. In humans, as well as dogs, AS specifically affects the glomerular basement membrane (GBM) of the kidney, causing a distinctive multilaminar splitting of the GBM ultrastructure, characteristic to the disease. These defects in the GBM contribute to the development of hematuria, proteinuria, and progressive renal injury which eventually lead to end stage renal disease (ESRD). Some human cases of AS have been reported to also be associated with hearing loss, ocular lesions and, in rare instances, leiomyomatosis.

The mutation in the COL4a4 gene causing ARAS and markers associated with ARAS are described above. As demonstrated above, genetic testing of COL4a4 facilitates identification of animals with ARAS. Since dogs with ARAS are similar in phenotype in many respects to human with ARAS, dogs with ARAS are candidate model systems for study of ARAS in humans. In addition, humans can also undergo genetic testing to determine if they are carriers of ARAS.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims. Those skilled in the art will recognize, or be able to ascertain using no more than routine experimentation, many equivalents to the specific embodiments of the invention described herein. Such equivalents are intended to be encompassed by the following claims.

We claim:

1. A method of detecting in a dog a mutation that causes autosomal recessive Alport Syndrome in English Cocker Spaniels comprising
   a) obtaining a biological sample from the dog;
   b) analyzing the biological sample for SEQ ID NO:90;
   wherein the presence of SEQ ID NO:90 is indicative of a dog carrying a mutation that causes Alport Syndrome in English Cocker Spaniels.

2. A method of detecting in a dog a mutation that causes autosomal recessive Alport Syndrome in English Cocker Spaniels comprising
   a) obtaining a biological sample from the dog;
   b) analyzing the biological sample for a single nucleotide polymorphism 93 bases upstream of exon 42 in canine COL4A4;
   wherein the presence of a T to A substitution 93 bases upstream of exon 42 in canine COL4A4 is indicative of a dog carrying a mutation that causes Alport Syndrome in English Cocker Spaniels.

3. A method of detecting in a dog a mutation that causes autosomal recessive Alport Syndrome in English Cocker Spaniels comprising
   a) obtaining a biological sample from the dog;
   b) analyzing the biological sample for a single polynucleotide polymorphism 90 bases upstream of exon 42 in canine COL4A4;
   wherein the presence of a T to C substitution 90 bases upstream of exon 42 in canine COL4A4 is indicative of a dog carrying a mutation that causes Alport Syndrome in English Cocker Spaniels.

4. A method of detecting in a dog a mutation that causes autosomal recessive Alport Syndrome in English Cocker Spaniels comprising
   a) obtaining a biological sample from the dog;
   b) analyzing the biological sample for a single polynucleotide polymorphism 32 bases upstream of exon 3 in canine COL4A4;
   wherein the presence of a T to C substitution 32 bases upstream of exon 3 in canine COL4A4 is indicative of a dog carrying a mutation that causes Alport Syndrome in English Cocker Spaniels.

* * * * *

```
                          SEQUENCE LISTING

<160> NUMBER OF SEQ ID NOS: 94

<210> SEQ ID NO 1
<211> LENGTH: 41
<212> TYPE: DNA
<213> ORGANISM: English Cocker Spaniel

<400> SEQUENCE: 1
ttcactttcc agagtggaaa gaagtttgtc ggccsctgtg g                    41

<210> SEQ ID NO 2
<211> LENGTH: 41
<212> TYPE: DNA
<213> ORGANISM: English Cocker Spaniel

<400> SEQUENCE: 2
ttcactttcc agagtggaaa gtagtttgtc ggccsctgtg g                    41

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
cagggcatag aacctcactt a                                          21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
aggcgaggca acagttacat a                                          21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ctgctgtgct ctggacatta g                                          21

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
```

-continued ccctggacca cctgcttac    19

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tcactaatga cagcagccta t    21

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
caaggtggca aagcaac    17

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
acctgggtaa cttggtaaga a    21

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcattctaca tttctaaggc    20

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
ccctctcacc aagccac    17

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
cgtcggttgc tggtact    17

<210> SEQ ID NO 13
<211> LENGTH: 23
<212> TYPE: DNA
<213> ORGANISM: Artificial Sequence -continued

```
<220> FEATURE:
<223> OTHER INFORMATION: Primer

<400> SEQUENCE: 13
gttgctgact gttgttagat gtt                                              23

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gctacttgtc attctgtgga g                                                21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
ggagtggaaa gaagtttgtc g                                                21

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
gatggatgtt gcttcgtg                                                    18

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
cctcgtgaac cattgtagcc                                                  20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ggatggacag tatcaggct                                                   19

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gagtcaccat tgccataacg                                                  20
```

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
gtcccacatc agacttcct                                            19

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
cagcctcctc ccacagtct                                            19

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
ctaaagcaga caccagcaa                                            19

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
gaaatctcca ctagcgaaac                                           20

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
tactgtgctg atactgtgct g                                         21

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
gcaagaacag ttaggagata ct                                        22

<210> SEQ ID NO 26
<211> LENGTH: 20
<212> TYPE: DNA
<213> ORGANISM: Artificial Sequence
<220> FEATURE:
<223> OTHER INFORMATION: Primer

```
<400> SEQUENCE: 26
gctggaactg gtattagatg                                          20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccacacagcc ttccacagtt                                          20

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
tatggcttag ggcaggaa                                            18

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
acccaggtaa tgccaaatga t                                        21

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
aagggcaatg atgtttacag a                                        21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
gatgtttctg ggactgtgat                                          20

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
cacctctaat actggagttg ta                                       22

<210> SEQ ID NO 33
```

```
<211> LENGTH: 19
<212> TYPE: DNA
<213> ORGANISM: Artificial Sequence
<220> FEATURE:
<223> OTHER INFORMATION: Primer

<400> SEQUENCE: 33
actggtaatg ggaggtgta                                            19

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
atgctaaatg tgcgtgct                                             18

<210> SEQ ID NO 35
<211> LENGTH: 15
<212> TYPE: DNA
<213> ORGANISM: Artificial Sequence
<220> FEATURE:
<223> OTHER INFORMATION: Primer

<400> SEQUENCE: 35
gaacccaggg caacc                                                15

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tgaagataaa ctataaagac aaat                                      24

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
ttaacatctg ctcctccat                                            19

<210> SEQ ID NO 38
<211> LENGTH: 16
<212> TYPE: DNA
<213> ORGANISM: Artificial Sequence
<220> FEATURE:
<223> OTHER INFORMATION: Primer

<400> SEQUENCE: 38
tggagcccaa cacaag                                               16

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
```

```
gccacgcagg attgtatg                                          18

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
caagggctga agttggaggt t                                      21

<210> SEQ ID NO 41
<211> LENGTH: 17
<212> TYPE: DNA
<213> ORGANISM: Artificial Sequence
<220> FEATURE:
<223> OTHER INFORMATION: Primer

<400> SEQUENCE: 41
gctgaggttg ctttggg                                           17

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
gagggatggg taggtctgag tg                                     22

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
gaagagataa tgtctgaaag atgta                                  25

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
aggtctaggg gataaaagtg                                        20

<210> SEQ ID NO 45
<211> LENGTH: 16
<212> TYPE: DNA
<213> ORGANISM: Artificial Sequence
<220> FEATURE:
<223> OTHER INFORMATION: Primer

<400> SEQUENCE: 45
cccaggtgcc ccaata                                            16

<210> SEQ ID NO 46
<211> LENGTH: 21
<212> TYPE: DNA
```

<213> ORGANISM: Artificial Sequence
<220> FEATURE:
<223> OTHER INFORMATION: Primer

<400> SEQUENCE: 46
ctgagtgaga gagaagagga a                                      21

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
gccataaagc agtttcataa g                                      21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
gagcgtgtta aataatagcc a                                      21

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
atctgtaaaa taaatgtgtc tcc                                    23

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
tcatcttcag tcctaataat agtcc                                  25

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
atgcgatact gagattttgc                                        20

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
gcagcaggtg gttggtctca gca                                    23

<210> SEQ ID NO 53
<211> LENGTH: 18
<212> TYPE: DNA
<213> ORGANISM: Artificial Sequence
<220> FEATURE:
<223> OTHER INFORMATION: Primer

<400> SEQUENCE: 53
gatacgaggt gatcccca                                         18

<210> SEQ ID NO 54
<211> LENGTH: 16
<212> TYPE: DNA
<213> ORGANISM: Artificial Sequence
<220> FEATURE:
<223> OTHER INFORMATION: Primer

<400> SEQUENCE: 54
ccacctgccg cattga                                           16

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gtcggattcc tttgtcattc                                       20

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
cccttcatct ctcgcttgc                                        19

<210> SEQ ID NO 57
<211> LENGTH: 18
<212> TYPE: DNA
<213> ORGANISM: Artificial Sequence
<220> FEATURE:
<223> OTHER INFORMATION: Primer

<400> SEQUENCE: 57
ccacccaagt cccatctc                                         18

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
gaacttgtgt ttcttcccct tac                                   23

<210> SEQ ID NO 59
<211> LENGTH: 18
<212> TYPE: DNA
<213> ORGANISM: Artificial Sequence
<220> FEATURE:

<223> OTHER INFORMATION: Primer

<400> SEQUENCE: 59
cagtgctgct ccaagttc                                                18

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
tgggttcagt ccatcaga                                                18

<210> SEQ ID NO 61
<211> LENGTH: 18
<212> TYPE: DNA
<213> ORGANISM: Artificial Sequence
<220> FEATURE:
<223> OTHER INFORMATION: Primer

<400> SEQUENCE: 61
ggtgagggtg aggctgtc                                                18

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
gaatagggtc ctcacataca g                                            21

<210> SEQ ID NO 63
<211> LENGTH: 18
<212> TYPE: DNA
<213> ORGANISM: Artificial Sequence
<220> FEATURE:
<223> OTHER INFORMATION: Primer

<400> SEQUENCE: 63
cggtttccat ttgtgtgc                                                18

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
ggatggggac ttagttatgt a                                            21

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
caggcttcat agaactgttt g                                            21

<210> SEQ ID NO 66
<211> LENGTH: 17
<212> TYPE: DNA
<213> ORGANISM: Artificial Sequence
<220> FEATURE:
<223> OTHER INFORMATION: Primer

<400> SEQUENCE: 66
aagcactcac gctctgg                                                        17

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
cttagagaga aagagtcata ggaa                                                24

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
ggactgttga gcattctttg                                                     20

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
aggagtgctc ataggcgta                                                      19

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
gcttacactg ccccatact                                                      19

<210> SEQ ID NO 71
<211> LENGTH: 16
<212> TYPE: DNA
<213> ORGANISM: Artificial Sequence
<220> FEATURE:
<223> OTHER INFORMATION: Primer

<400> SEQUENCE: 71 cccccccaaca gaccat                                                        16

<210> SEQ ID NO 72
<211> LENGTH: 19
<212> TYPE: DNA
<213> ORGANISM: Artificial Sequence
<220> FEATURE:
<223> OTHER INFORMATION: Primer -continued

```
<400> SEQUENCE: 72
ctcgggctca gggtctaac                                              19

<210> SEQ ID NO 73
<211> LENGTH: 18
<212> TYPE: DNA
<213> ORGANISM: Artificial Sequence
<220> FEATURE:
<223> OTHER INFORMATION: Primer

<400> SEQUENCE: 73
cagcactgag aacagcac                                               18

<210> SEQ ID NO 74
<211> LENGTH: 16
<212> TYPE: DNA
<213> ORGANISM: Artificial Sequence
<220> FEATURE:
<223> OTHER INFORMATION: Primer

<400> SEQUENCE: 74
ggctgcggat cagtgc                                                 16

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
aggtcaagag cctcagtttt at                                          22

<210> SEQ ID NO 76
<211> LENGTH: 18
<212> TYPE: DNA
<213> ORGANISM: Artificial Sequence
<220> FEATURE:
<223> OTHER INFORMATION: Primer

<400> SEQUENCE: 76
ctcctcctct ctggctcc                                               18

<210> SEQ ID NO 77
<211> LENGTH: 22
<212> TYPE: DNA
<213> ORGANISM: Artificial Sequence
<220> FEATURE:
<223> OTHER INFORMATION: Primer

<400> SEQUENCE: 77
gaaatgtgaa cagcaaggaa ta                                          22

<210> SEQ ID NO 78
<211> LENGTH: 25
<212> TYPE: DNA
<213> ORGANISM: Artificial Sequence
<220> FEATURE:
<223> OTHER INFORMATION: Primer

<400> SEQUENCE: 78
taaaatgttg atgaatctgt aaaat                                       25

<210> SEQ ID NO 79
<211> LENGTH: 20
```

```
<212> TYPE: DNA
<213> ORGANISM: Artificial Sequence
<220> FEATURE:
<223> OTHER INFORMATION: Primer

<400> SEQUENCE: 79
gtcctgtgtt tcctcctact                                          20

<210> SEQ ID NO 80
<211> LENGTH: 18
<212> TYPE: DNA
<213> ORGANISM: Artificial Sequence
<220> FEATURE:
<223> OTHER INFORMATION: Primer

<400> SEQUENCE: 80
ggaggcgtgt ctgtgggt                                            18

<210> SEQ ID NO 81
<211> LENGTH: 19
<212> TYPE: DNA
<213> ORGANISM: Artificial Sequence
<220> FEATURE:
<223> OTHER INFORMATION: Primer

<400> SEQUENCE: 81
ccaaagatgg ctctgatta                                           19

<210> SEQ ID NO 82
<211> LENGTH: 21
<212> TYPE: DNA
<213> ORGANISM: Artificial Sequence
<220> FEATURE:
<223> OTHER INFORMATION: Primer

<400> SEQUENCE: 82
ccgtgtctca agaggctatg g                                        21

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
ggtttgctat tgagtaactg tcta                                     24

<210> SEQ ID NO 84
<211> LENGTH: 21
<212> TYPE: DNA
<213> ORGANISM: Artificial Sequence
<220> FEATURE:
<223> OTHER INFORMATION: Primer

<400> SEQUENCE: 84
gttggttctt ccctggataa t                                        21

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
```

-continued

```
ttattgaacg gttctgctgt a                                              21

<210> SEQ ID NO 86
<211> LENGTH: 22
<212> TYPE: DNA
<213> ORGANISM: Artificial Sequence
<220> FEATURE:
<223> OTHER INFORMATION: Primer

<400> SEQUENCE: 86
aactggagtc tgaaatgagc ac                                             22

<210> SEQ ID NO 87
<211> LENGTH: 19
<212> TYPE: DNA
<213> ORGANISM: Artificial Sequence
<220> FEATURE:
<223> OTHER INFORMATION: Primer

<400> SEQUENCE: 87
aggcagttca aatcgtctc                                                 19

<210> SEQ ID NO 88
<211> LENGTH: 22
<212> TYPE: DNA
<213> ORGANISM: Artificial Sequence
<220> FEATURE:
<223> OTHER INFORMATION: Primer

<400> SEQUENCE: 88
aactattggt tcatcatctt ac                                             22

<210> SEQ ID NO 89
<211> LENGTH: 71
<212> TYPE: DNA
<213> ORGANISM: English Cocker Spaniel

<400> SEQUENCE: 89
actaaaccag atgcttcact ttccagagtg gaaagaagtt tgtcggcccc tgtggaggaa    60
gagattgctc g                                                         71

<210> SEQ ID NO 90
<211> LENGTH: 71
<212> TYPE: DNA
<213> ORGANISM: English Cocker Spaniel

<400> SEQUENCE: 90
actaaaccag atgcttcact ttccagagtg gaaagtagtt tgtcggcccc tgtggaggaa    60
gagattgctc g                                                         71

<210> SEQ ID NO 91
<211> LENGTH: 74
<212> TYPE: DNA
<213> ORGANISM: English Cocker Spaniel

<400> SEQUENCE: 91
cctcaaagta ttatgtataa ttctcgaata accgattttg cttttgccct aactgacaaa    60
tttaaaatct cttt                                                      74

<210> SEQ ID NO 92
<211> LENGTH: 74
<212> TYPE: DNA
<213> ORGANISM: English Cocker Spaniel
```

```
<400> SEQUENCE: 92
cctcaaagta ttatgtataa ttctcgaata accgaattcg cttttgccct aactgacaaa    60
tttaaaatct cttt                                                       74

<210> SEQ ID NO 93
<211> LENGTH: 71
<212> TYPE: DNA
<213> ORGANISM: English Cocker Spaniel

<400> SEQUENCE: 93
tgtacacatc atgtgcccag ctcagtgtgc aatactggtt tactaaacca gatgcttcac    60
tttccagagt g                                                          71

<210> SEQ ID NO 94
<211> LENGTH: 71
<212> TYPE: DNA
<213> ORGANISM: English Cocker Spaniel

<400> SEQUENCE: 94
tgtacacatc atgtgcccag ctcagtgtgc aataccggtt tactaaacca gatgcttcac    60
tttccagagt g                                                          71
```